(12) United States Patent  (10) Patent No.: US 7,469,033 B2
Kulik et al.  (45) Date of Patent: Dec. 23, 2008

(54) DENSITY MEASUREMENT WITH GAMMA BACKSCATTERING

(75) Inventors: Alex Kulik, Sugar Land, TX (US); Nikolay Baturin, Sugar Land, TX (US); Alexander Joseph Esin, Cedar Park, TX (US); Michael Masterov, Houston, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 0 days.

(21) Appl. No.: 11/598,559

(22) Filed: Nov. 13, 2006

(65) Prior Publication Data

US 2008/0112536 A1  May 15, 2008

(51) Int. Cl.
   *G01B 15/02* (2006.01)
(52) U.S. Cl. .......................... 378/54; 378/57
(58) Field of Classification Search .................... 378/51, 378/54, 57, 59, 58
   See application file for complete search history.

(56) References Cited

U.S. PATENT DOCUMENTS

| 3,832,545 | A | * | 8/1974 | Bartko | 376/159 |
| 4,817,021 | A | * | 3/1989 | Sowerby et al. | 702/137 |
| 2006/0133566 | A1 | * | 6/2006 | Li et al. | 378/57 |

* cited by examiner

*Primary Examiner*—Courtney Thomas
(74) *Attorney, Agent, or Firm*—Osha Liang LLP (57) ABSTRACT

A system for measuring the density of a fluid in a vessel, the system including: at least one gamma-ray source positioned proximate to the vessel; at least one gamma-ray detector positioned proximate to the vessel, wherein the at least one gamma-ray detector is configured to detect gamma rays backscattered by the fluid from the at least one gamma-ray source; and a translator for converting the detected gamma-ray backscatter to a density value. A method to determine properties of a fluid in a vessel, the method including: positioning a gamma-ray source proximate to the vessel; positioning a gamma-ray detector proximate to the vessel; detecting gamma rays backscattered by the fluid from the gamma-ray source with the gamma-ray detector; determining a density of the fluid based upon an intensity of backscattered gamma rays received by the gamma-ray detector.

20 Claims, 5 Drawing Sheets

DENSITY MEASUREMENT WITH GAMMA BACKSCATTERING

BACKGROUND OF INVENTION

1. Field of the Invention

Embodiments disclosed herein relate generally to the measurement of the density of a fluid in a vessel using gamma radiation. Specifically, embodiments disclosed herein relate to the measurement of the density of a fluid in a vessel by detecting the intensity of gamma rays backscattered by the fluid from a gamma-ray source.

2. Background

Gamma rays have been used to measure the density and level of fluids in a vessel by using a gamma-ray source positioned opposite a gamma-ray detector. These through-transmission gamma-ray density and level measurements are useful where the materials measured are hazardous, extremely hot, or where direct contact measurements are otherwise not possible. Additionally, the source and detector are mounted outside the vessel, and no modification to the vessel is required. Gamma rays emitted by a source may be absorbed or attenuated by the vessel and the material in the vessel. The strength of the gamma radiation reaching a detector opposite the source may be used to indicate the density or level of a fluid in a vessel based upon the intensity of the source.

When measuring fluid level, for example, multiple gamma-ray emitters and/or detectors may be positioned at opposite sides of a vessel, where the presence or absence of a signal (or a nominal low signal) may indicate the presence or absence of a fluid in place between the source and detector. The size of a vessel in a signal/no signal level detector may be much larger than that for a gamma-ray densitometer, as described below, as gamma rays are not as readily absorbed or attenuated by vapors in the vessel.

With respect to fluid density, for example, fluid passing between the gamma-ray source and detector may absorb or attenuate gamma rays emitted by the source. A high radiation count indicates a low fluid density while a low count indicates high fluid density.

Figure 1:
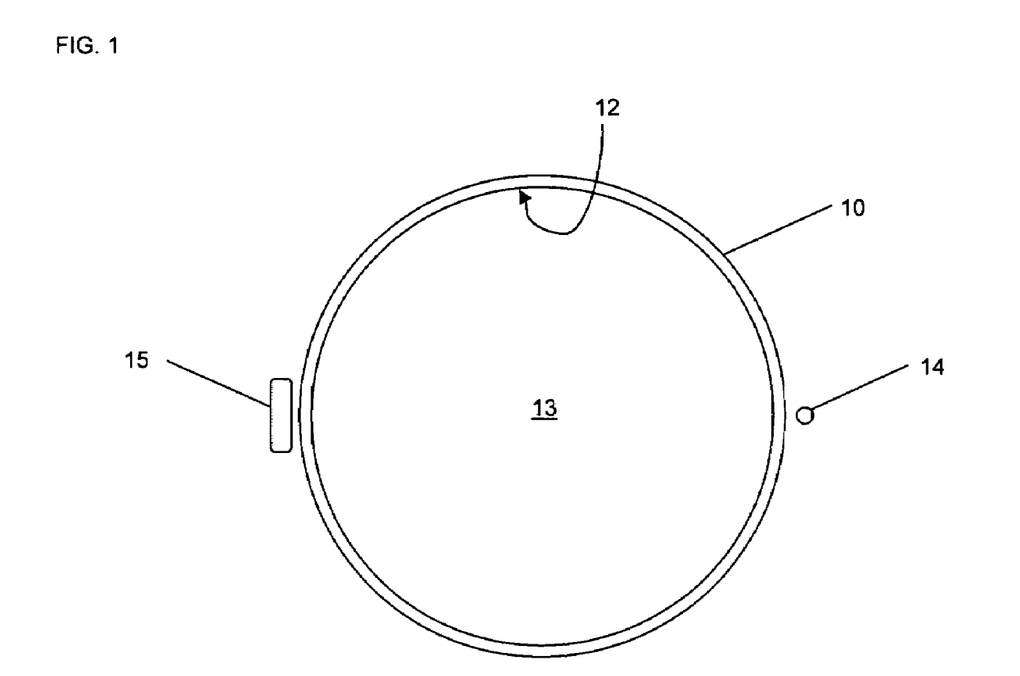
FIG. 1 is a simplified schematic drawing of a prior-art through-transmission gamma-ray densitometer.

Referring now to FIG. 1, one example of a prior-art through-transmission gamma-ray densitometer is illustrated. A housing (not shown) may be mounted on a tubular pipe or vessel 10 with a bore 12 which contains a fluid 13. A source of gamma radiation 14 is located on one side of the bore 12 and, a gamma radiation detector 15 is located on an opposite side. The radiation provided by the source 14 is a constant intensity over a long period of time (random intensity over a finite period) of gamma-ray emissions. The gamma rays are transmitted through the material surrounding the bore 12, the fluid 13 within the bore and to the detector 15. The detector 15 may be, for example, a crystal of sodium or cesium iodide (thallium activated) or other material capable of scintillating under irradiation and may include an electron photomultiplier tube for converting light flashes of the scintillation of the crystal into an electrical pulse.

A primary variable with respect to the amount of gamma rays emitted from source 14 that reach detector 15 is fluid 13 contained within vessel 10. A percentage of the gamma rays emitted by source 14 are absorbed or attenuated by fluid 13 and do not reach detector 15. Thus, the counting rate of the output signal from the photo multiplier tube of detector 15 may be related to the density of fluid 13 through which the rays must pass to reach detector 15 and the intensity of source 14.

However, through-transmission density measurement using gamma rays is viable only for limited vessel sizes and/or fluid densities. For example, for a similar sized source, at higher fluid densities, the fluid may absorb more gamma rays, thus resulting in fewer gamma rays reaching the detector. Similarly, as vessel size is increased, gamma rays must pass through a greater quantity of material (vessel and fluid) absorbing the gamma rays, resulting in fewer gamma rays reaching the detector. Therefore, gamma-ray density measurements in this manner are currently only viable for vessels up to about 1 meter in diameter.

Vessel thickness may also limit the effectiveness of through-transmission gamma-ray density measurements. As vessels absorb and attenuate gamma rays in a manner similar to fluids, and a higher wall thickness may result in fewer gamma rays reaching the detector. Vessel thickness may be regulated by code, such as ASME or other vessel specifications, where the required thickness may be based upon operating pressure and the nature of the fluid (corrosive, erosive, reactive, etc.). Furthermore, current safety margins for vessel thickness may increase and may further limit the effectiveness of through-transmission measurements.

Another disadvantage in the present use of gamma rays for through-transmission density measurements is that the solid angle subtended by a fixed size detector, and thus the counting rate, scales inversely with the size of the vessel squared. The counting rate n may be approximated by the equation:

$$n \sim \Omega e^{-d/\lambda} \sim (e^{-d/\lambda})/d^2 \quad (1)$$

where n is the counting rate, d is the vessel diameter, and $\lambda$ is the absorption length which depends on density. For a similar sized detector, a lower count rate may result in a greater rate of error or may require a larger source to maintain a desired accuracy. Alternatively, as vessel size is increased, detector size may be increased to maintain a constant count rate. Regardless, increasing the size of the source and/or the size of the detector will invariably increase costs.

To overcome the thickness, size, and density limitations, the intensity of the gamma-ray source may be increased, thus resulting in a measurable quantity of gamma rays reaching the detector. However, cost, safety, multi-unit effectiveness, and security may each limit the source intensity that may be used. For example, the use of a radioactive source creates personnel safety and environmental concerns and requires lead or tungsten shielding to protect personnel, special handling precautions and equipment, as well as disposal and remediation procedures. Furthermore, because gamma rays are produced from a point source and not a directional source, as the size of the source increases, the amount of shielding required to contain the radiation in directions other than through the vessel must be increased, thus adding further to the cost.

With respect to multi-unit effectiveness, a chemical plant may desire to use gamma-ray level and density gages on multiple vessels, for example. However, as the number of gages is increased or the intensity of gamma-ray sources is increased to overcome size limitations, cross-talk between gamma-ray sources and detectors on adjacent vessels may occur, resulting in decreased effectiveness and potentially erroneous readings.

Regarding security, due to growing worldwide concerns about the proliferation and possible smuggling or other transport of radioactive nuclear materials, state, local, and national governments regulate facility security requirements based upon the total amount of radioactive material that may be present at a single site. For example, the State of Texas requires additional security measures (e.g., background checks, accessibility, etc.) at facilities where the total Curie count exceeds 27 Curie, where the total Curie count is based upon a sum of all radioactive sources at the facility. Thus, use of larger sources to overcome vessel size limitations may result in an increased need for security at an additional cost.

Accordingly, there exists a need for gamma-ray density gages that may be used on larger vessels. Additionally, there exists a need for non-contact density gages that require lower intensity radiation sources.

SUMMARY OF INVENTION

In one aspect, embodiments disclosed herein relate to a system for measuring the density of a fluid in a vessel, the system including: at least one gamma-ray source positioned proximate to the vessel; at least one gamma-ray detector positioned proximate to the vessel, wherein the at least one gamma-ray detector is configured to detect gamma rays backscattered by the fluid from the at least one gamma-ray source; and a translator for converting the detected gamma-ray backscatter to a density value.

In another aspect, embodiments disclosed herein relate to a method to determine properties of a fluid in a vessel, the method including: positioning a gamma-ray source proximate to the vessel; positioning a gamma-ray detector proximate to the vessel; detecting gamma rays backscattered by the fluid from the gamma-ray source with the gamma-ray detector; determining a density of the fluid based upon an intensity of backscattered gamma rays received by the gamma-ray detector.

In another aspect, embodiments disclosed herein relate to a method to control a density of a fluid in a vessel, wherein the vessel forms one component in a process, the method including: positioning a gamma-ray source proximate to the vessel; positioning a gamma-ray detector proximate to the vessel; detecting gamma-rays backscattered by the fluid from the gamma-ray source with the gamma-ray detector; determining a density of the fluid based upon an intensity of backscattered gamma rays received by the gamma-ray detector; and adjusting at least one process variable to manipulate the density.

Other aspects and advantages of the invention will be apparent from the following description and the appended claims.

DETAILED DESCRIPTION

In one aspect, embodiments disclosed herein relate to measurement of the density of a fluid in a vessel using gamma rays. In other aspects, embodiments disclosed herein relate to measurement of the density of a fluid in a vessel using gamma rays where the vessel is greater than 1 meter in diameter. In particular, embodiments disclosed herein relate to measurement of the density of a fluid in a vessel by detecting the intensity of gamma rays backscattered by the fluid from a gamma-ray source.

As used herein, "backscatter" may refer to the deflection of gamma rays from the original direction. In some embodiments, the backscatter may be isotropic, such as where the gamma rays are scattered randomly in various directions. Backscattering occurs due to Compton scattering.

As used herein, "fluid" refers to gases, liquids, and solids that may be contained within a vessel. Fluids may include aqueous liquids, organic liquids, single-phase systems, and multi-phase systems such as foams, emulsions, and fluidized particles.

As used herein, "diameter" refers to the effective diameter of a pipe or vessel, regardless of vessel or pipe geometry. Although the specification and figures indicate cylindrical vessels, one skilled in the art would appreciate that the gamma-ray backscatter measurement systems described herein may be used with vessels and pipes of other geometries.

Figure 2:
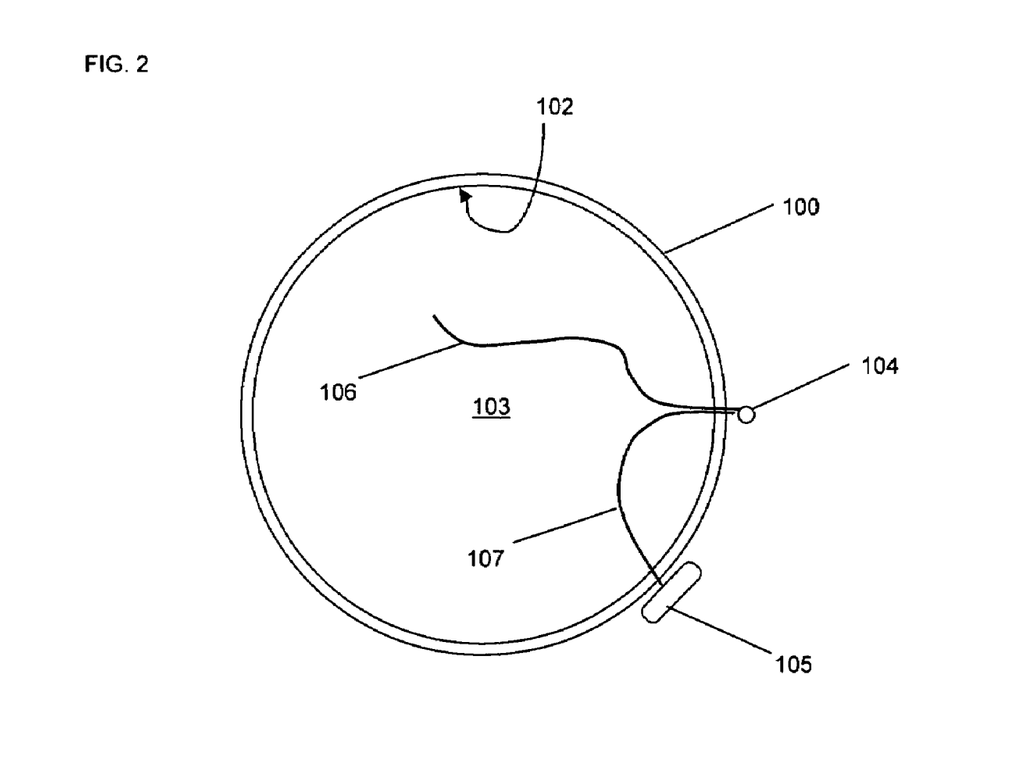
FIG. 2 is a schematic drawing of a gamma-ray density measurement system according to embodiments disclosed herein.

Referring now to FIG. 2, one example of a gamma-ray densitometer is illustrated. A tubular pipe or vessel 100 may have a bore 102 through which a fluid 103 is caused to flow. At least one source of gamma radiation 104 may be located proximate to pipe or vessel 100, and a gamma radiation detector 105 may be positioned to detect gamma rays backscattered from the at least one gamma-ray source 104.

A percentage of the gamma rays emitted by the gamma-ray source 104 may be absorbed or attenuated by the vessel 100 and the fluid 103 and do not reach the gamma-ray detector 105. For example, a gamma ray may follow path 106, undergoing one or more scatterings off an atomic electron, eventually being absorbed or dissipating in energy, failing to reach detector 105.

A portion of the gamma rays emitted by source 104 may be deflected, with or without attenuation, thus reaching detector 105. For example, a gamma ray may follow path 107, undergoing one or more scatterings, eventually reaching detector 105. The rate at which gamma rays reach detector 105 may be related to the density of fluid 103 through which the gamma rays must pass to reach the detector 105 and the intensity of the source 104.

Figure 4:
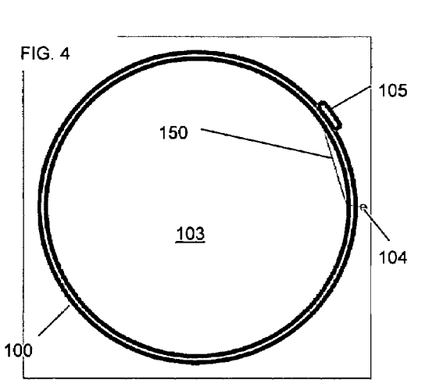
FIG. 4 is a schematic drawing depicting one potential path a backscattered gamma ray may take in reaching a gamma-ray detector according to embodiments disclosed herein.
Figure 5:
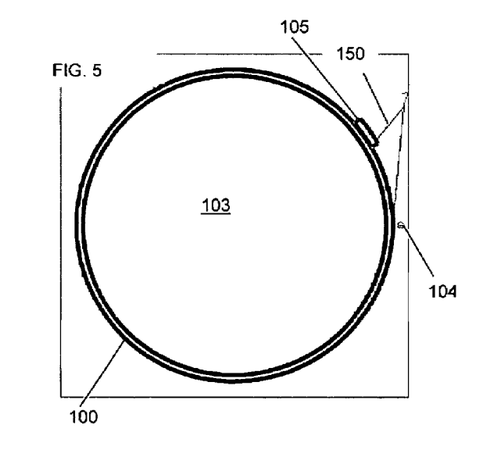
FIG. 5 is a schematic drawing depicting one potential path a backscattered gamma ray may take in reaching a gamma-ray detector according to embodiments disclosed herein.
Figure 6:
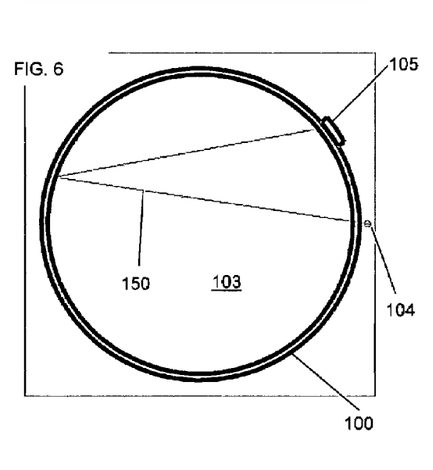
FIG. 6 is a schematic drawing depicting one potential path a backscattered gamma ray may take in reaching a gamma-ray detector according to embodiments disclosed herein.

Referring now to FIGS. 3-6, gamma rays may reach the detector through various mechanisms. Gamma rays may travel varied paths 150, which may be roughly categorized as follows: scattering in the fluid (FIG. 3); scattering in the vessel walls (FIG. 4); scattering outside the vessel (FIG. 5); scattering from the opposite wall (FIG. 6). Scattering from the opposite wall, as illustrated in FIG. 6, generally happens only at very low fluid densities, such as through air, for example.

Figure 3:
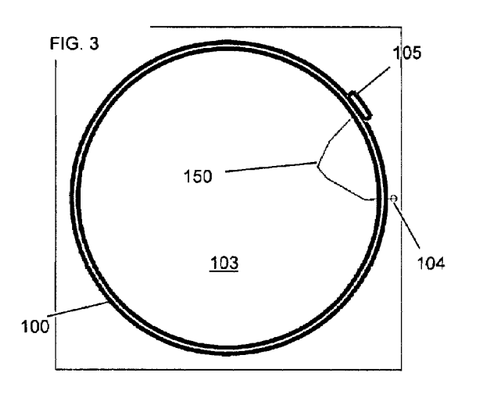
FIG. 3 is a schematic drawing depicting one potential path a backscattered gamma ray may take in reaching a gamma-ray detector according to embodiments disclosed herein.

Scattering from outside the vessel, as illustrated in FIG. 5, may be a significant portion of the total gamma-ray count for high density fluids (sand), and may also be considerable for intermediate density fluids. Scattering in the walls, as illustrated in FIG. 4, may occur for low density fluids, but is typically not present for high density fluids. Scattering in the material, as illustrated in FIG. 3, is dominant for intermediate density fluids (0.2-0.8 g/cc).

Gamma-ray backscatter measured by the detector may include each of the above described backscatter events in some embodiments. In other embodiments, shielding may be used to prevent or minimize the amount of backscatter from one or more events other than scattering from the fluid. For example, the source, the detector, or both, may be appropriately shielded to prevent scatter from outside the vessel reaching a detector.

Figure 7:
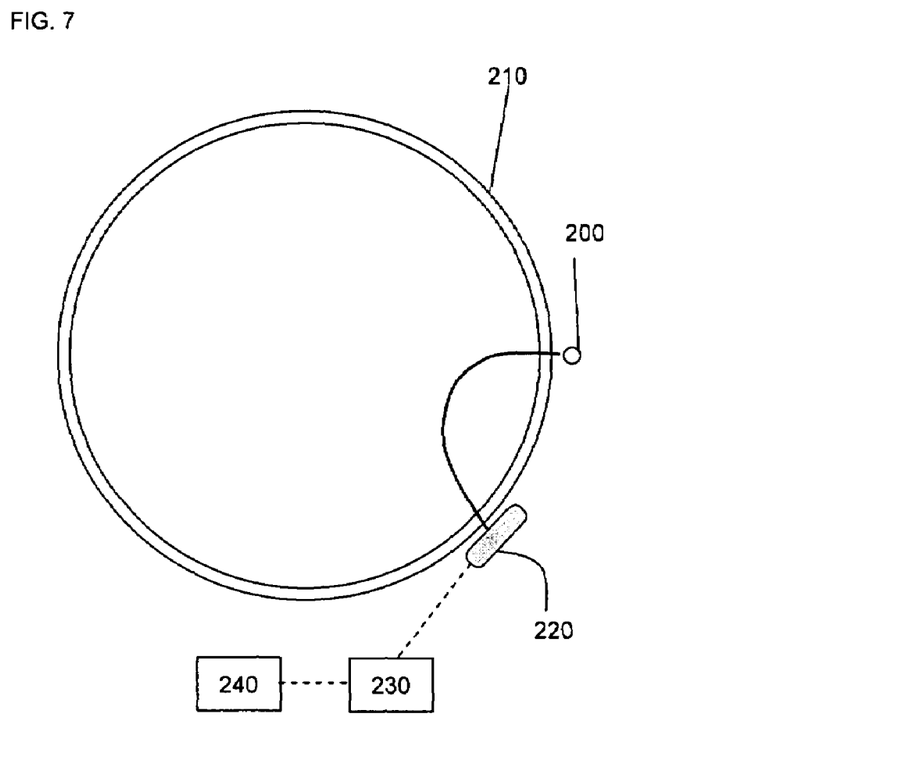
FIG. 7 is a schematic drawing of a gamma-ray density measurement system according to embodiments disclosed herein.

Referring now to FIG. 7, one embodiment of the gamma-ray backscatter density meter coupled to a computer or a digital control system ("DCS") is illustrated. One or more gamma-ray sources 200 may be distributed along the circumference of or distributed axially along the height of vessel or pipe 210. One or more gamma-ray detectors 220 may be positioned relative to the sources 200 to detect gamma rays backscattered from the corresponding source. Use of multiple sources and/or detectors may allow for a more accurate determination of fluid density as will be described below.

The one or more detectors may be coupled to a rate meter 230. Rate meter 230 may convert pulses of energy produced by detectors 220 to a DC signal which is proportional to the gamma-ray detection rate. The rate at which the gamma rays are detected will be a function of the density of the fluid proximate the detector 230 and the corresponding source 200. The DC signals may be interpolated using a computer or DCS 240, generating a display of the calculated density value corresponding to the measured detection rate of gamma-ray backscatter.

Fluid density may vary within the interior of pipe or vessel 200, radially and/or axially. The limited vicinity over which a backscatter meter as described herein may measure density may not always provide an accurate representation of the bulk fluid density, such as where flow turbulence does not provide for a well mixed fluid. Where more than one detector 230 is placed along vessel 210, the interpolated density values returned by DCS 240 may be averaged. The averaged density value may be a more accurate representation of fluid density as the multiple detectors only measure the density of the fluid in a limited vicinity proximate the source(s) and the detectors.

Figure 8:
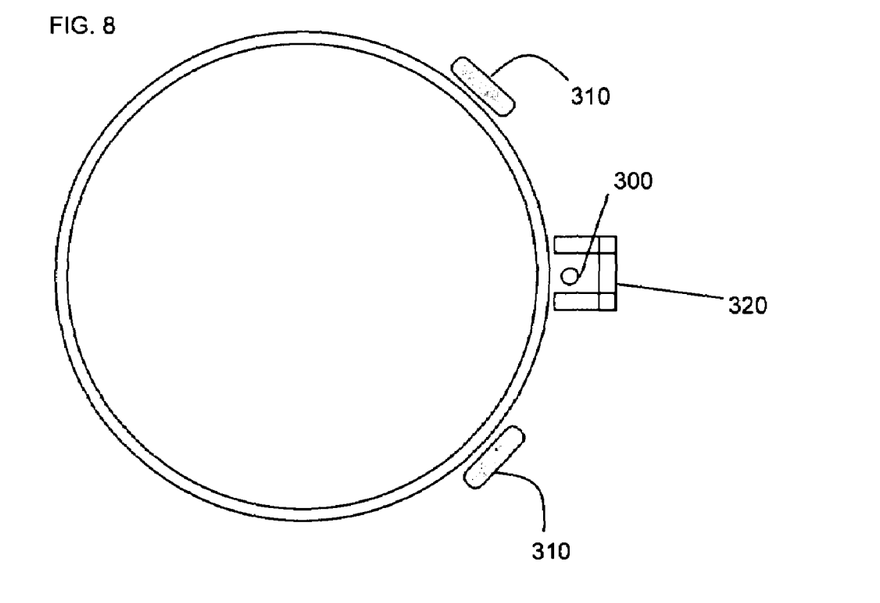
FIG. 8 is a schematic drawing of a gamma-ray density measurement system using two detectors and one source spaced circumferentially according to embodiments disclosed herein.
Figure 9A:
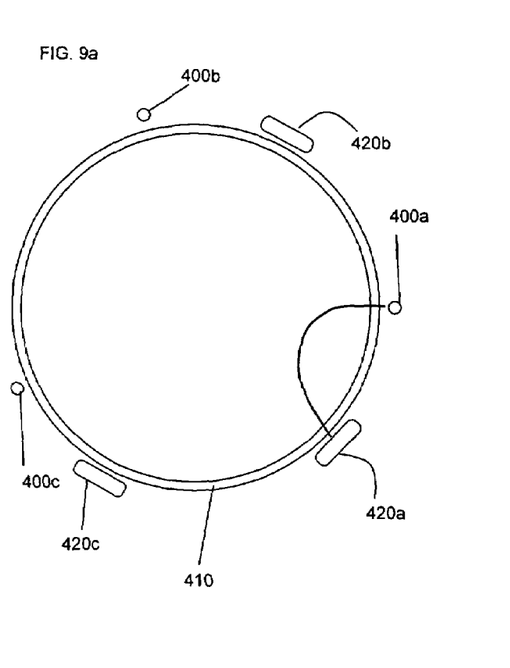
FIGS. 9a-9b present schematic drawings of a gamma-ray density measurement system using multiple detectors and multiple sources spaced axially according to embodiments disclosed herein.
Figure 9B:
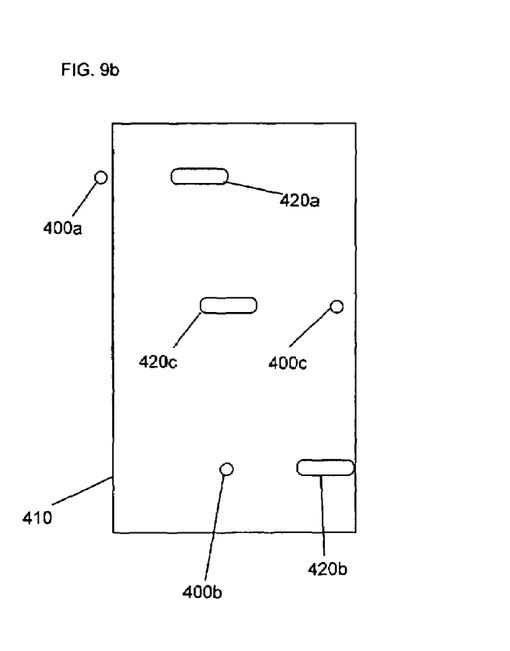

Referring now to FIGS. 8 and 9a-9b, density measurement systems are illustrated where one or more sources are combined with one or more detectors to provide multiple measurements of the density of a fluid within a vessel or pipe. As illustrated in FIG. 8, a gamma-ray source 300 may be spaced circumferentially from two gamma-ray detectors 310. Shielding 320 may be provided between gamma-ray source 300 and gamma-ray detectors 310. In this manner, density measurements may be obtained for the fluid in two areas of the vessel 330 using only one gamma-ray source 300. Alternatively, or cooperatively with circumferentially spaced gamma-ray detectors 310, gamma-ray detectors may be spaced circumferentially or axially from gamma-ray source 300 to provide density measurements for the fluid in the vessel 330.

As illustrated in FIGS. 9a (top view) and 9b (profile view), multiple gamma-ray sources 400 may be positioned axially and circumferentially along vessel or pipe 410. One or more gamma-ray detectors 420 correspondingly located to measure backscatter of gamma rays from gamma-ray source 400. Shielding (not shown) may be provided to minimize crosstalk between the various gamma-ray sources and detectors. Additionally, based upon working fluid density and the vessel diameter, the detectors may be spaced such that transmission and/or backscatter from one gamma-ray source to a gamma-ray detector is minimized or avoided.

As described above, the gamma-ray detectors may be positioned to detect gamma rays backscattered from a gamma-ray source. In some embodiments, gamma-ray detectors may be positioned relative to a gamma-ray source so as to detect gamma rays backscattered from a gamma-ray source, and positioned such that through-transmission gamma rays reaching the detector are minimal or non-existent.

Figure 10A:
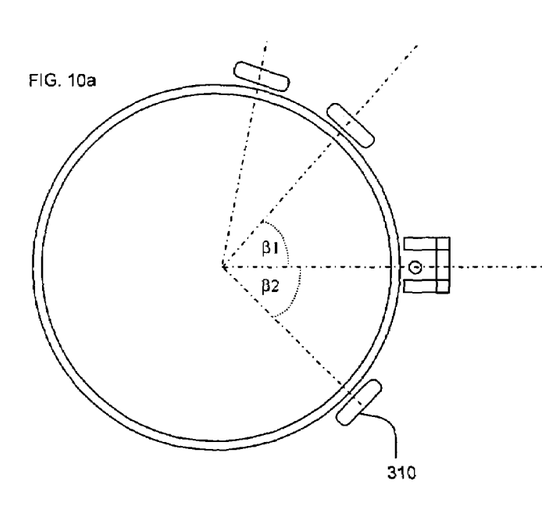
FIGS. 10a-10b present schematic drawings of a gamma-ray density measurement system using multiple detectors spaced at varied angles from a gamma-ray source according to embodiments disclosed herein.

In selected embodiments, a gamma-ray source may be spaced circumferentially from a corresponding gamma-ray detector, where the angle $\beta$ ($\beta 1$ or $\beta 2$) between gamma-ray source and gamma-ray detector may be 90 degrees or less, as illustrated in FIG. 10a. The angle $\beta$ may be 75 degrees or less in other embodiments; 60 degrees or less in other embodiments; 45 degrees or less in other embodiments; 30 degrees or less in other embodiments; and 15 degrees or less in yet other embodiments.

Figure 10B:
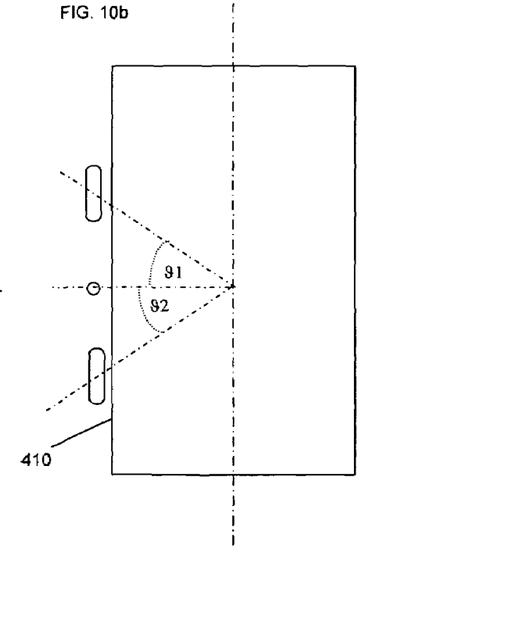

In some embodiments, a gamma-ray detector may be spaced axially from a corresponding gamma-ray detector, where the angle $\vartheta$ ($\vartheta 1$ or $\vartheta 2$) may be 60 degrees or less, as illustrated in FIG. 10b. The angle $\vartheta$ may be 45 degrees or less in other embodiments; 30 degrees or less in other embodiments; and 15 degrees or less in yet other embodiments.

Where more than one gamma-ray detector is placed relative to a corresponding gamma-ray source, the angles $\vartheta$, $\beta$ between the source and the corresponding detectors may be the same or different, such as angles $\beta 1$ and $\beta 2$ illustrated in FIG. 10a and angles $\vartheta 1$ and $\vartheta 2$ in FIG. 10b. In some embodiments, the multiple gamma-ray detectors may be placed on the same side of the gamma-ray source; in other embodiments, gamma-ray detectors may be placed on opposite sides of the gamma-ray source.

In addition to obtaining an average density value, as described above, use of multiple detectors along the circumference or height/length of pipe or vessel 200 may be used to generate a profile of a fluid in pipe or vessel 200. For example, as illustrated in FIGS. 9a and 10a, circumferentially spaced detectors may provide an indication of a density variance between angular sections of pipe or vessel 200, such as a quadrant or an octant. As another example, as illustrated in FIGS. 9b and 10b, axially spaced detectors may provide an indication of an axial density gradient.

Measurement of axial and/or radial density gradients may provide an indication of the degree of settling or mixing that may be occurring in vessel or pipe 200. For example, an axial density gradient may indicate the degree of settling of a solid from a suspension contained in a vessel 200. As another example, various radial density gradients may be indicative of static, laminar, or turbulent flow in a pipe 200. Where pipe or vessel 200 forms a component in a process, one or more process variables may be manipulated in response to the density profile, such as to increase mixing or to decrease settling rates, for example.

The source of gamma rays may include cesium-137, americium-241, radium-226, iridium-192, and cobalt-60. In some embodiments, the activity of the source may range from 0.1 mCi to 10 Ci. In other embodiments, the activity of the source may be less than 5 Ci; less than 2 Ci in other embodiments; and less than 1 Ci in yet other embodiments.

Due to the measurement of backscatter as opposed to conventional through-transmission, the activity of the source may be minimized while providing density measurement of a fluid in a vessel. In some embodiments, a similar size source may be used for vessels ranging in size from 1 meter to 10 meters in diameter. In other embodiments, a similar size source may be used for vessels ranging in wall thickness from 0.01 inches to 6.0 inches or more.

In selected embodiments, density measurements may be obtained by gamma-ray backscattering by irradiating a vessel having a diameter of greater than 1.5 meters with one or more gamma-ray sources having an intensity of less than 2 Ci; less than 1 Ci in other embodiments; less than 500 mCi in other embodiments; less than 100 mCi in other embodiments; and less than 10 mCi in yet other embodiments. In other embodiments, density measurements may be obtained by gamma-ray backscattering by irradiating a vessel having a diameter of greater than 3 meters with one or more gamma-ray sources having an intensity of less than 2 Ci; less than 1 Ci in other embodiments; less than 500 mCi in other embodiments; less than 100 mCi in other embodiments; and less than 10 mCi in yet other embodiments.

Gamma-ray detectors useful in embodiments disclosed herein may include scintillators such as sodium iodide, cesium iodide, and plastic scintillators. In some embodiments, gamma-ray detectors may include electron photo multiplier tubes. In other embodiments, gamma-ray detectors may include plastic scintillators, such as a polyvinyl toluene (PVT) scintillator, for example. In yet other embodiments, gamma-ray detectors may include ionization chambers, Geiger counters, proportional counters, semiconductors or other detectors suitable for detection of gamma rays. Where embodiments of the density measurement system disclosed herein contain more than one detector, the detectors may be of the same or different types of gamma-ray detectors.

Gamma-ray backscatter density meters in accordance with embodiments disclosed herein may measure the density of a fluid in a vessel, where the density of the fluid may range from 0.05 g/cc to 7.0 g/cc. The effective density range may be from 0.1 g/cc to 4.0 g/cc in other embodiments; and from 0.2 to 2.0 g/cc in yet other embodiments. In other embodiments, one or more gamma-ray backscatter density meters may be used in conjunction with one or more gamma-ray through-transmission density meters.

In yet other various embodiments, the density of a fluid in a pipe or vessel may be controlled by manipulating one or more process variables based upon the measured density. For example, where a pipe or vessel forms a component in a process, one or more process variables may be manipulated in response to the gamma-ray backscatter density measurement of the fluid in the pipe or vessel.

The gamma-ray backscatter density gages described above may be used to measure the density of a fluid in a vessel. Prior to use of the gage during operation or production, the gamma-ray backscatter gage may be calibrated. Multiple fluids of known density may be passed through a vessel, where the same vessel or a similar to the vessel for which the gage will measure the density of the contents during operation. Gamma-ray counts for the known density fluids may be determined and recorded, developing a density calibration curve (count profile). Then, when used during production or operation, measured gamma-ray counts may be compared to the density calibration curve to determine the density of the fluid; the density of the fluid may be interpolated based upon the intensity of the backscattered gamma rays.

EXAMPLES

Simulation of Gamma-Ray Backscattering

The count rate (percentage of gamma rays reaching the detector) as a function of the fluid density may be simulated for a particular vessel material and geometry, and fluid composition, wherein a Monte Carlo simulation of the Compton scattering of the gamma rays is performed and returns the count rate for an input fluid.

Figure 11:
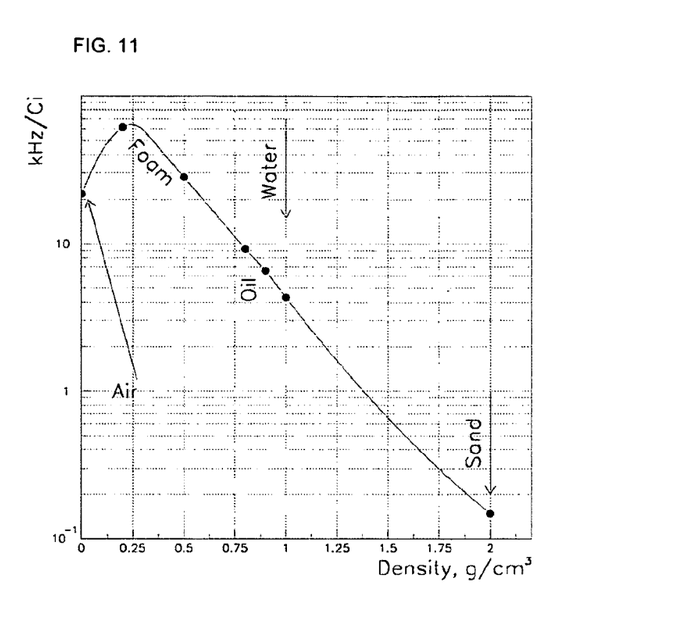
FIG. 11 is a chart depicting the rate of backscatter gamma-ray detection for various fluids based upon Monte Carlo simulations of embodiments of the gamma-ray density measurement system disclosed herein.

Referring now to FIG. 11, the simulated count rate as a function of density for a cylindrical vessel having a 2 meter diameter, 2 meters in height, with 4 cm thick steel walls is presented for a simulation using a 1 Ci $^{137}$Cs source and a 20×20 cm detector. Simulation results indicated that sand, water, heavy and light oil, and heavy and light foam may be clearly identified by gamma-ray backscattering count rates.

Figure 12A:
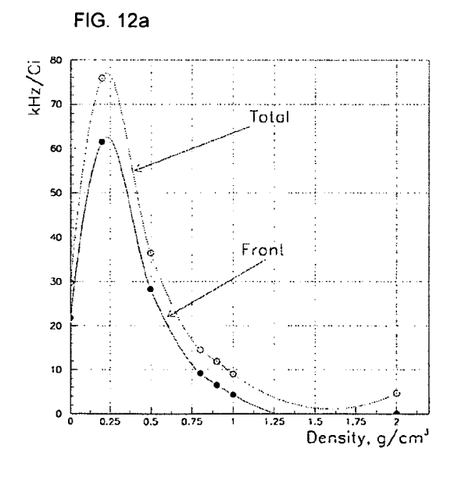
FIGS. 12a-12b are charts depicting the rate of backscatter gamma-ray detection for various fluids based upon Monte Carlo simulations of embodiments of the gamma-ray density measurement system disclosed herein.
Figure 12B:
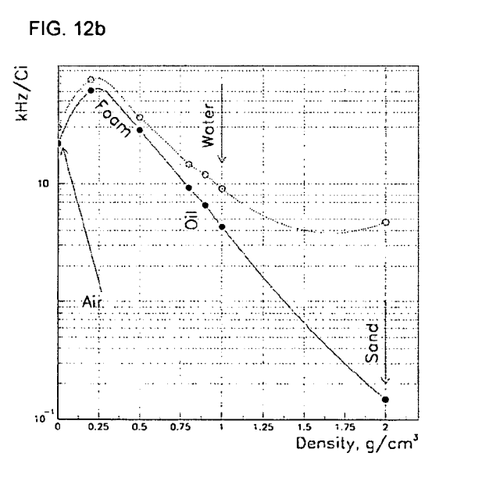

As described above, several backscatter events may cause gamma rays to enter the detector from its back and sides, such as through scattering outside the vessel. Again, the simulation was performed for a 1 Ci $^{137}$Cs source and a 20×20 cm detector. As shown in FIG. 12a (linear scale) and 12b (log scale), simulated results for the total rate (upper line) and the rate coming only from the front of the counter (bottom line) are illustrated. The unwanted backscatter count, or the difference in total count rate and count from the front of the detector, may be a considerable fraction of the total count, especially at high density.

Unwanted scatter events may be blocked by shielding the back and sides of the counter. Shielding the source may also effectively minimize count due to unwanted scatter. Shielding of both the source and the detector may also be done to minimize count due to unwanted scatter.

Laboratory Tests

The validity of the simulation and the operational principle as a whole was tested in laboratory by altering a bucket of water and the same bucket filled with either pulverized coal or hydraulic oil. Although the measured signal ratios are not as large as in FIGS. 12a-12b, they are consistent with the ratios predicted in simulation.

In the test, a 5 mCi $^{137}$Cs source was used to irradiate a 5 gallon bucket filled with a fluid. A PVT plastic scintillator was used to detect the scattered radiation, and was placed relative to the source so as to detect gamma-ray backscatter. Sufficient shielding was placed intermediate the source and the detector to prevent transmission of gamma rays from the source to the detector, the detector count thus including only backscatter radiation. Fluids used included water, pulverized coal (from Southern Company Services, bulk density of 0.7 g/cc) and hydraulic oil (from Golden West, density of 0.9 g/cc). The buckets were filled with the desired fluid, and the count rates were measured.

In the first run, the gamma-ray detector was placed approximately at the mid height of the bucket and about 1 inch away from the bucket. In the second run, the counter was placed toward the top of the bucket and as close to the bucket as possible. The results of the first and second runs are presented in Table 1 below.

TABLE 1

| Material | Measured Count Rate (kHz/Ci) |
|---|---|
| Run 1 | |
| Water | 11.40 |
| Coal | 10.66 |
| Run 2 | |
| Water | 18.64 |
| Oil | 19.34 |
| Coal | 17.62 |

The results of the first and second runs indicate that gamma-ray backscatter may be effectively used to determine the density of a fluid in a vessel. The results of the first and second runs are compared to the Monte Carlo simulation results in Table 2 below.

TABLE 2

| Materials | Measured Count Ratio | Simulated Count Ratio |
|---|---|---|
| Coal Water | 0.935; 0.945 Average: 0.940 | 0.911 ± 0.02 |
| Oil Water | 1.038 | 1.054 ± 0.017 |

The comparison of simulated results to the results of the first and second runs indicated that the measured results were within two standard deviations of the simulated results. These results may differ due to the variation in vessel composition and thickness (bucket versus 2 cm steel) as well as the relative placement of the source and the detector. Additionally, simulated and actual results may differ due to the variation in the simulated and actual chemical compositions of the coal and oil.

As illustrated by the above simulations and experiments, vessel size, material, and source/detector placement may each affect the gamma-ray backscatter count rate. Accordingly, calibration curves generated prior to operational use for each source/detector/vessel combination may provide for accurate measurement of fluid densities during operation.

Advantageously, embodiments disclosed herein may provide for non-contact density measurement by positioning a gamma-ray detector relative to a gamma-ray source so as to detect gamma-ray backscatter. The non-contact measurement may allow for the measurement of density where the material is hazardous, extremely hot, or where direct contact measurements are not possible. By detecting gamma-ray backscatter, gamma rays do not have to traverse the entire vessel diameter, which may allow for the use of lower intensity gamma-ray sources as well as measurement of density in larger vessels than is current possible with through-transmission measurements.

Because embodiments of the gamma-ray backscatter density measurements described herein may allow for use of lower intensity gamma-ray sources, cross-talk between multiple meters used within a production facility may be decreased. The use of lower intensity sources may also allow for use of more than one source and/or detector per vessel, possibly generating a more accurate reflection of fluid density due to multiple measurements. Additionally, because backscatter measurement may allow use of lower intensity gamma-ray sources, production facilities may use additional measuring devices at a single site without incurring the more stringent safety protocols required by state and federal governments for sites having moderate amounts of radioactive material.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for measuring the density of a fluid, the system comprising:
    a vessel having the fluid disposed therein;
    at least one gamma-ray source positioned proximate to the vessel;
    a plurality of gamma-ray detectors positioned proximate to the vessel and disposed circumferentially about the vessel with respect to each other, wherein the plurality of gamma-ray detectors are configured to detect gamma rays backscattered by the fluid from the at least one gamma-ray source; and
    a translator for converting the detected gamma-ray backscatter to a density value.

2. The system for measuring density of claim 1, wherein the translator comprises:
    a device to convert the detected gamma rays to a DC signal; and
    a computer for convening the DC signal to a density value.

3. The system for measuring density of claim 2, further comprising a display console for displaying the DC signal, the density value, or a combination thereof.

4. The system for measuring density of claim 2, wherein the computer receives a DC signal from multiple detectors and determines an average density.

5. The system for measuring density of claim 1, wherein the source and detector are separated at an angle of 60 degrees or less.

6. The system for measuring density of claim 1, wherein the gamma-ray source is selected from the group consisting of cesium-137 and cobalt-60.

7. The system for measuring density of claim 1, wherein the at least one gamma-ray detector comprises at least one of a sodium iodide scintillator, a cesium iodide scintillator, a plastic scintillator, a Geiger counter, a proportional counter, a semiconductor, and an ionization detector.

8. The system for measuring density of claim 1, wherein the system comprises a single gamma-ray source and at least two gamma-ray detectors.

9. The system for measuring density of claim 1, wherein the system comprises at least two gamma-ray sources and at least two gamma-ray detectors.

10. The system for measuring density of claim 1, wherein the vessel is greater than 3.0 meters in diameter and an intensity of the gamma-ray source is less than 1 Ci.

11. The system for measuring density of claim 1, wherein the vessel is substantially formed of steel and comprises a wall thickness of at least about 4.0 cm (1.6 in).

12. The system for measuring density of claim 1, wherein the plurality of gamma-ray detectors are axially disposed along a length of the vessel with respect to each other.

13. The system for measuring density of claim 1, wherein the vessel is equal to or greater than 1.5 meters in diameter and an intensity of the gamma-ray source is equal to or less than 1 Ci.

14. A method to determine properties of a fluid, the method comprising:

positioning a gamma-ray source proximate to a vessel, wherein the vessel has the fluid disposed therein;

positioning a plurality of gamma-ray detectors proximate to the vessel such that the plurality of gamma-ray detectors are circumferentially disposed about the vessel with respect to each other;

detecting gamma rays backscattered by the fluid from the gamma-ray source with the plurality of gamma-ray detectors; and determining a density of the fluid based upon an intensity of backscattered gamma rays received by the plurality of gamma-ray detectors.

15. The method of claim 14, further comprising generating a calibration curve for use in the determination of the fluid density.

16. The method of claim 14, wherein the determining comprises interpolating a density based upon a calibration curve.

17. The method of claim 14, further comprising converting the detected gamma-ray backscatter to a DC signal.

18. The method of claim 17, further comprising converting the DC signal to a density value.

19. The method of claim 18, further comprising displaying at least one of the DC signal and the density value on a video display terminal.

20. A method to control a density of a fluid during a process, the method comprising:

positioning a gamma-ray source proximate to a vessel, wherein the vessel has the fluid disposed therein;

positioning a plurality of gamma-ray detectors proximate to the vessel such that the plurality of gamma-ray detectors are circumferentially disposed about the vessel with respect to each other;

detecting gamma-rays backscattered by the fluid from the gamma-ray source with the plurality of gamma-ray detectors;

determining a density of the fluid based upon an intensity of backscattered gamma rays received by the plurality of gamma-ray detectors; and adjusting at least one process variable to manipulate the density of the fluid.

* * * * *